(12) United States Patent
Bihorac et al.

(10) Patent No.: US 12,340,905 B2
(45) Date of Patent: Jun. 24, 2025

(54) SYSTEMS AND METHODS FOR USING DEEP LEARNING TO GENERATE ACUITY SCORES FOR CRITICALLY ILL OR INJURED PATIENTS

(71) Applicant: UNIVERSITY OF FLORIDA RESEARCH FOUNDATION, INCORPORATED, Gainesville, FL (US)

(72) Inventors: Azra Bihorac, Gainesville, FL (US); Tyler J. Loftus, Gainesville, FL (US); Tezcan Ozrazgat Baslanti, Gainesville, FL (US); Parisa Rashidi, Gainesville, FL (US); Benjamin P. Shickel, Alachua, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 26 days.

(21) Appl. No.: 17/309,975

(22) PCT Filed: Feb. 21, 2020

(86) PCT No.: PCT/US2020/019331
§ 371 (c)(1),
(2) Date: Jul. 7, 2021

(87) PCT Pub. No.: WO2020/172607
PCT Pub. Date: Aug. 27, 2020

(65) Prior Publication Data
US 2022/0044809 A1 Feb. 10, 2022

Related U.S. Application Data

(60) Provisional application No. 62/809,159, filed on Feb. 22, 2019.

(51) Int. Cl.
*G16H 50/20* (2018.01)
*G06N 3/084* (2023.01)
(Continued)

(52) U.S. Cl.
CPC ............ *G16H 50/20* (2018.01); *G16H 10/60* (2018.01); *G16H 50/30* (2018.01); *G16H 50/50* (2018.01); *G06N 3/084* (2013.01)

(58) Field of Classification Search
CPC ........ G16H 50/20; G16H 10/60; G16H 50/30; G16H 50/50; G06N 3/084; G06N 3/0481;
(Continued)

(56) References Cited

U.S. PATENT DOCUMENTS

2012/0191630 A1* 7/2012 Breckenridge ........ G06N 20/00
706/12
2017/0235910 A1 8/2017 Cantillon et al.
(Continued)

FOREIGN PATENT DOCUMENTS

WO WO-2018/210646 A1 11/2018
WO WO-2019/178524 A1 9/2019

OTHER PUBLICATIONS

Benjamin Shickel, Tyler J. Loftus, LasithAdhikari, Tezcan Ozrazgat-Baslanti, Azra Bihorac & Parisa Rashidi, "DeepSOFA: A Continuous Acuity Score for Critically Ill Patients using Clinically Interpretable Deep Learning" Scientific Reports Published online: Feb. 12, 2019 (Year: 2019).*
(Continued)

*Primary Examiner* — Gregory D. Moseley
(74) *Attorney, Agent, or Firm* — Alston & Bird LLP

(57) ABSTRACT

Methods, apparatus, systems, and computer program products for providing patient predictions are provided in various embodiments. Responsive to receiving an indication of initiation of a patient interaction, a model for the patient is
(Continued)

initiated by an assessment computing entity. The model has been trained using machine learning and the model is configured to generate a prediction for the patient. The prediction comprises at least one of an acuity score or a mortality prediction. Responsive to identifying a prediction trigger, the assessment computing entity updates the model for the patient based at least in part on medical data corresponding to the patient. The assessment computing entity generates the prediction using the updated deep learning model. The assessment computing entity provides at least a portion of the prediction such that the at least a portion of the prediction may be used to update an electronic health record corresponding to the patient and/or provided to a clinician for review.

20 Claims, 7 Drawing Sheets

(51) Int. Cl.
  *G16H 10/60* (2018.01)
  *G16H 50/30* (2018.01)
  *G16H 50/50* (2018.01)

(58) Field of Classification Search
  CPC ........ G06N 5/003; G06N 7/005; G06N 20/20; G06N 3/0445; G06N 3/044; G06N 3/048; G06N 5/01; G06N 7/01
  See application file for complete search history.

(56) References Cited

U.S. PATENT DOCUMENTS

| | | | |
|---|---|---|---|
| 2018/0158552 A1* | 6/2018 | Liu | G06N 3/0454 |
| 2019/0034591 A1* | 1/2019 | Mossin | G06N 3/08 |
| 2019/0354836 A1* | 11/2019 | Shah | G06N 3/045 |
| 2020/0034718 A1* | 1/2020 | Beedu | G06F 3/0653 |
| 2020/0132861 A1* | 4/2020 | Kim | G06N 3/0454 |
| 2020/0139973 A1* | 5/2020 | Palanisamy | G08G 1/167 |
| 2020/0176115 A1* | 6/2020 | Winslow | G16H 50/30 |

OTHER PUBLICATIONS

The supplemental information referenced in the Shickel publication available at http://static-content.springer.com/esm/art%3A10.1038%2Fs41598-019-38491-0/MediaObjects/41598_2019_38491_MOESM1_ESM.pdf (Year: 2019).*

Yao Qin, et al., "A Dual-Stage Attention-Based Recurrent Neural Network for Time Series Prediction", Proceedings of the Twenty-Sixth International Joint Conference on Artificial Intelligence (IJCAI-17) Aug. 2017, p. 2627-33 (Year: 2017).*

International Searching Authority, International Search Report and Written Opinion for International Application No. PCT/US2020/019331, dated May 11, 2020, (14 pages), United States Patent and Trademark Office, USA.

* cited by examiner

| Model | Training Required? | Mortality Probability Prediction at Hour T | AUC Calculation at Hour T |
|---|---|---|---|
| DeepSOFA | Yes | Feed current data sequence from hour 0 to hour T through RNN to get mortality probability prediction. | Get mortality probability predictions at hour T for all ICU encounters in validation cohort. For ICU encounters already completed by hour T, use final mortality prediction. Calculate AUC between mortality probability predictions and true in-hospital mortality labels. |
| Bedside SOFA | No | Calculate SOFA score for previous 24-hour period (T-24, T]. Consult published mortality rate table relating SOFA score to overall mortality rate. Use mortality rate as patient mortality probability prediction. | Calculate SOFA score for previous 24-hour period (T-24, T] for all ICU encounters in validation cohort. For ICU encounters already completed by hour T, use final SOFA score. Calculate AUC between SOFA scores and true in-hospital mortality labels. |
| Traditional SOFA | | N/A | |

FIG. 6

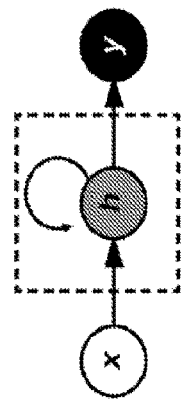

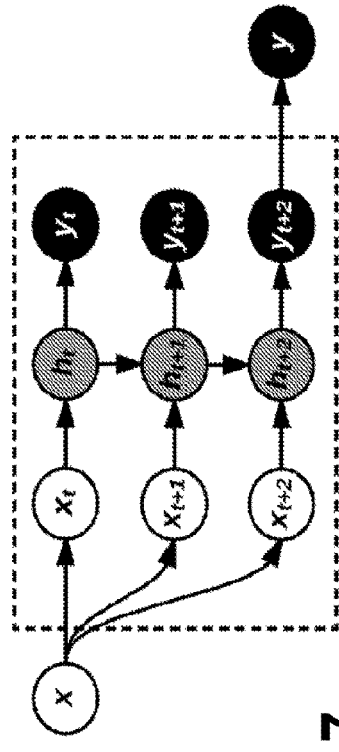

FIG. 7

SYSTEMS AND METHODS FOR USING DEEP LEARNING TO GENERATE ACUITY SCORES FOR CRITICALLY ILL OR INJURED PATIENTS

CROSS-REFERENCE TO RELATED APPLICATIONS

This application is a National Stage Application, filed under 35 U.S.C. § 371, of International Application No. PCT/US2020/019331, filed Feb. 21, 2020, which claims priority to U.S. Application No. 62/809,159, filed Feb. 22, 2019, the contents of both of which are incorporated herein by reference in their entireties.

FEDERALLY SPONSORED RESEARCH OR DEVELOPMENT

This invention was made with government support under Grant No. 1750192 awarded by the National Science Foundation and Grant Nos. GM111152 and GM110240 awarded by the National Institutes of Health. The government has certain rights in the invention.

BACKGROUND

Patients experiencing a medical event (e.g., critically ill and/or injured patients, such as patients in the intensive care unit (ICU), patients undergoing a surgical procedure, and/or the like), may have a life-threatening condition or the propensity to develop one at any moment. Early recognition of evolving illness severity in critically ill patients and/or evolving severity of patient condition is invaluable. Timely and accurate illness and/or patient condition severity assessments may identify patients in need of life-saving interventions prior to the occurrence of an unexpected adverse event and may inform shared decision-making processes among patients, providers, and families regarding goals of care and optimal resource utilization.

One of the most commonly used tools for assessing ICU patient acuity is the Sequential Organ Failure Assessment (SOFA) score. SOFA considers variables representing six different organ systems (cardiovascular, respiratory, nervous, liver, coagulation, and renal) and uses their worst measurements over a given interval (typically 24 hours) in conjunction with static value thresholds to assign numerical scores for each component. The sum of these component scores yields the overall SOFA score, which can be used to assess illness severity and predict mortality. Although SOFA provides a reasonably accurate assessment of a patient's overall condition and mortality risk, its accuracy is hindered by fixed cutoff points for each component score, and SOFA variables are often infrequent or missing in electronic health records. In particular, Glasgow Coma Scale scores and measurements of serum bilirubin and partial pressure of arterial oxygen are often sparse. Additionally, the complexity of determining a patient's SOFA score hinders the (near) real time determination of a SOFA scores for patients.

BRIEF SUMMARY OF SOME EXAMPLE EMBODIMENTS

Various embodiments of the present invention provide methods, apparatus, systems, computer program products, and/or the like for acuity monitoring and/or mortality prediction for patients undergoing medical events (e.g., an ICU admission/stay, a medical/surgical procedure, and/or the like). For example, an example embodiment may periodically (e.g., once minutes, once an hour, and/or the like) provide an acuity score, mortality prediction, one or more self-attention parameters and/or distributions, and/or the like for a patient undergoing a medical event (e.g., a patient admitted to the ICU, a patient undergoing a surgical procedure, and/or the like) for the extent of the medical event (e.g., the extent of the patient's ICU stay, through completion of a surgical procedure, through a patient's stay in the recovery room after a surgical procedure, and/or the like). In an example embodiment, the provided acuity score, mortality prediction, one or more self-attention parameters and/or distributions are provided in (near) real-time and/or indicate which of the one or more self-attention parameters and/or distributions represent therapeutic targets that may be used to efficiently and/or effectively improve the patient's acuity score and/or mortality prediction. In various embodiments, the acuity score, mortality prediction, and/or one or more self-attention parameters and/or distributions are determined by a deep learning model. In an example embodiment, the deep learning model is a modified recurrent neural network (RNN) with gated recurrent units (GRU) and a self-attention mechanism. In various embodiments, the acuity score, mortality prediction, and/or one or more self-attention parameters and/or distributions are generated by a deep learning model that comprises a static module for receiving and processing static and/or background information/data corresponding to the patient and a time series module for receiving and processing time series of biometric measurements and/or the like corresponding to the patient through the medical event.

According to a first aspect, a method for providing a patient prediction during a medical event, for example, is provided. In an example embodiment, the method comprises, responsive to receiving an indication of initiation of a medical event corresponding to a patient, initiating a deep learning model for the patient. The deep learning model comprises a modified recurrent neural network (RNN) with gated recurrent units (GRUs) and is executed by an assessment computing entity. The deep learning model has been trained using machine learning. The deep learning model is configured to generate a prediction for the patient, wherein the prediction comprises at least one of an acuity score or a mortality prediction. The method further comprises, responsive to identifying a prediction trigger, automatically updating, by the assessment computing entity, the deep learning model for the patient based at least in part on medical data corresponding to the patient. The medical data is captured during the medical event as part of one or more time series of medical data. The method further comprises automatically generating, by the assessment computing entity, the prediction using the updated model; and automatically providing, by the assessment computing entity, at least a portion of the prediction such that the at least a portion of the prediction may be used to update an electronic health record corresponding to the patient and/or provided to a clinician for review.

According to another aspect, an apparatus specially configured to provide a patient prediction during a medical event, for example, is provided. In an example embodiment, the apparatus comprises at least one processor, a communications interface configured for communicating via at least one network, and at least one memory storing computer program code. The at least one memory and the computer program code are configured to, with the processor, cause the apparatus to at least responsive to receiving an indication of initiation of a medical event corresponding to a patient, initiate a deep learning model for the patient; responsive to identifying a prediction trigger, automatically update the deep learning model for the patient based at least in part on medical data corresponding to the patient; automatically generate the prediction using the updated model; and automatically provide at least a portion of the prediction such that the at least a portion of the prediction may be used to update an electronic health record corresponding to the patient and/or provided to a clinician for review. The deep learning model comprises a modified recurrent neural network (RNN) with gated recurrent units (GRUs) and is executed by the at least one processor of the apparatus. The deep learning model has been trained using machine learning. The deep learning model is configured to generate a prediction for the patient, wherein the prediction comprising at least one of an acuity score or a mortality prediction. The medical data is captured during the medical event as part of one or more time series of medical data.

According to yet another aspect, a computer program product configured to cause an apparatus to provide a patient prediction during a medical event, for example, is provided. In an example embodiment, the computer program product comprises at least one non-transitory computer-readable storage medium having computer-readable program code portions stored therein. The computer-readable program code portions comprise executable portions configured, when executed by a processor of an apparatus, to cause the apparatus to, responsive to receiving an indication of initiation of a medical event corresponding to a patient, initiate a deep learning model for the patient; responsive to identifying a prediction trigger, automatically update the deep learning model model for the patient based at least in part on medical data corresponding to the patient; automatically generate the prediction using the updated model; and automatically provide at least a portion of the prediction such that the at least a portion of the prediction may be used to update an electronic health record corresponding to the patient and/or provided to a clinician for review. The deep learning model comprises a modified recurrent neural network (RNN) with gated recurrent units (GRUs) and is executed by the processor of the apparatus. The deep learning model has been trained using machine learning. The deep learning model is configured to generate a prediction for the patient, wherein the prediction comprising at least one of an acuity score or a mortality prediction. The medical data is captured during the medical event as part of one or more time series of medical data.

BRIEF DESCRIPTION OF THE DRAWINGS

Figure 1:
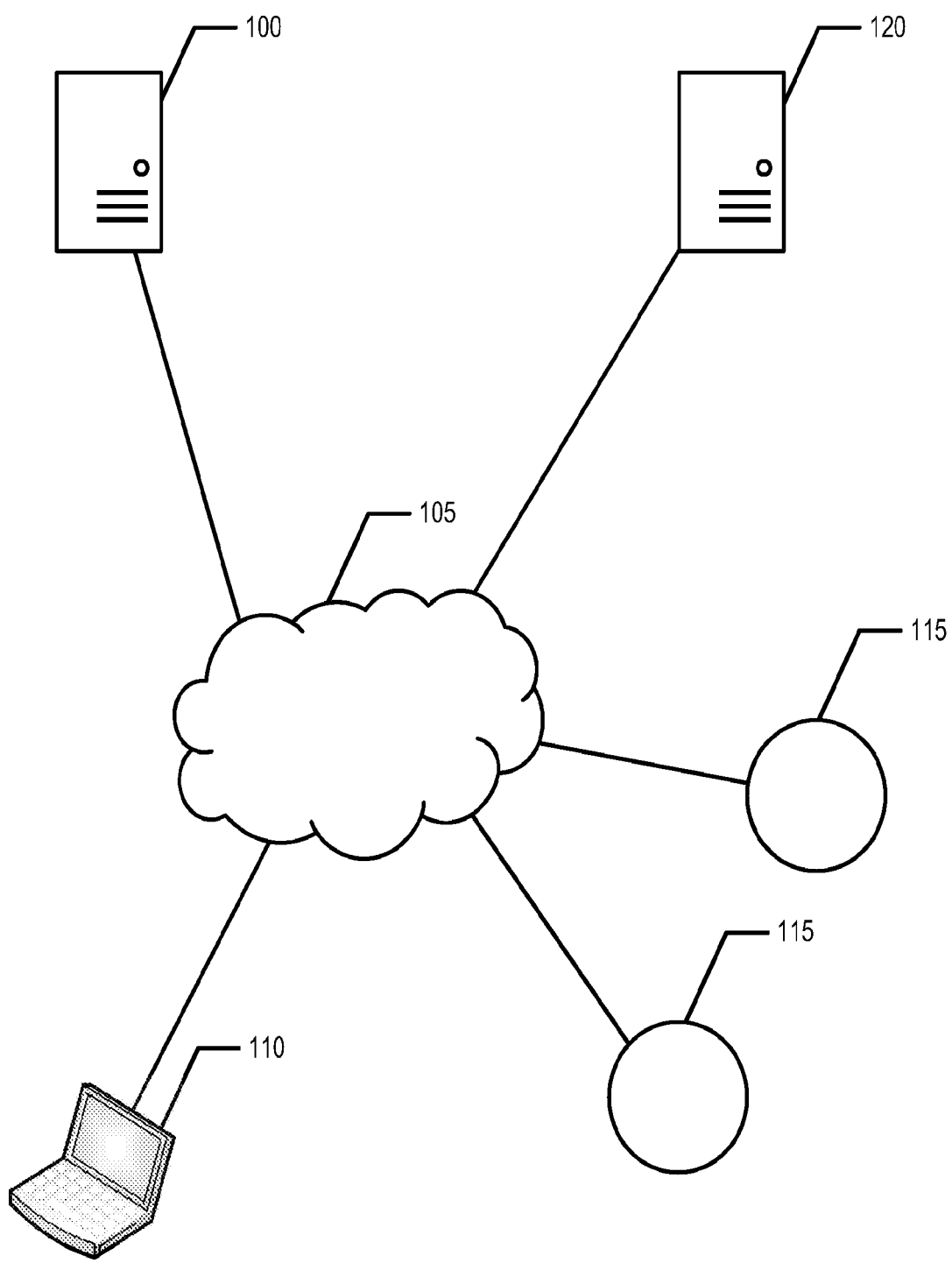

Having thus described the invention in general terms, reference will now be made to the accompanying drawings, which are not necessarily drawn to scale, and wherein:

FIG. 1 is an overview of a system that can be used to practice embodiments of the present invention.

Figure 2:
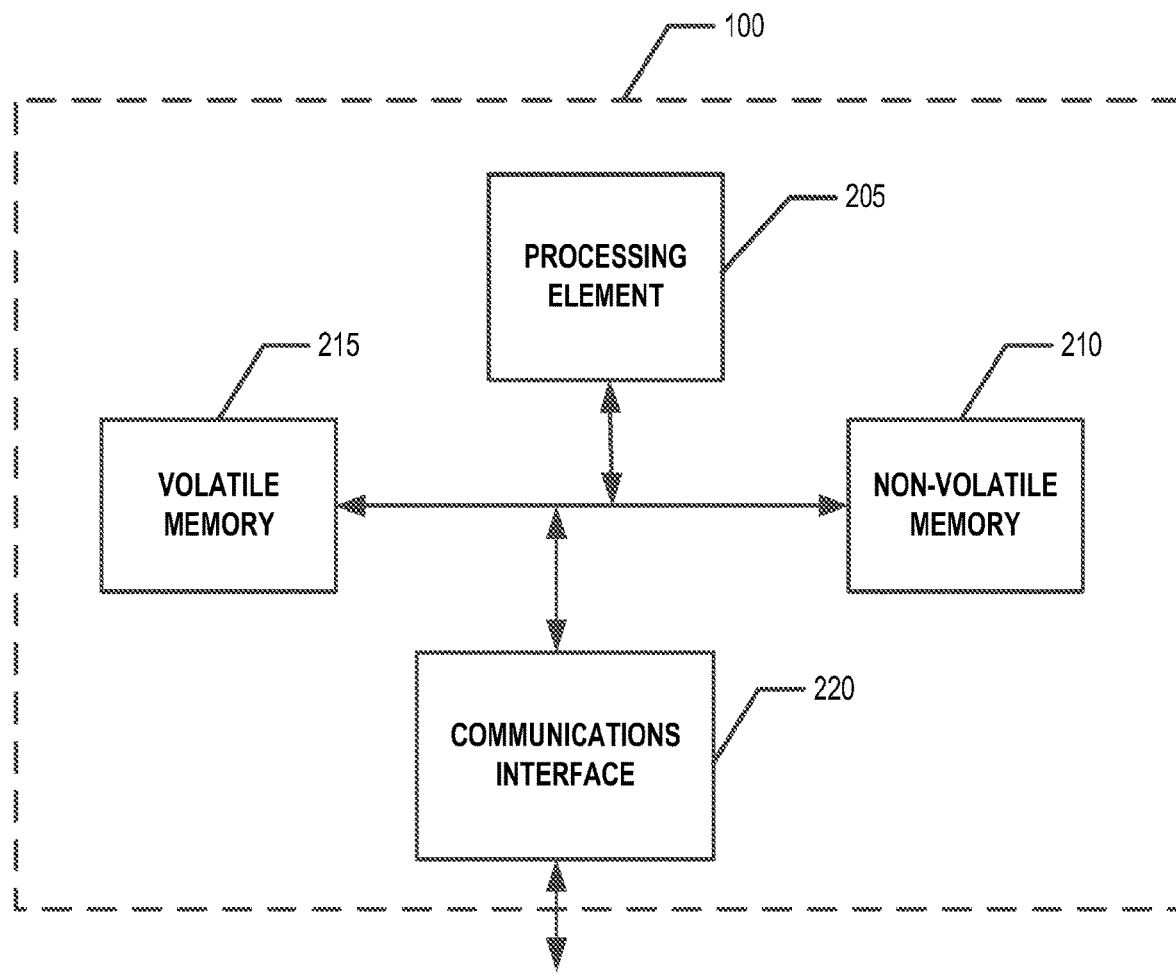

FIG. 2 is an exemplary schematic diagram of an assessment computing entity according to one embodiment of the present invention.

Figure 3:
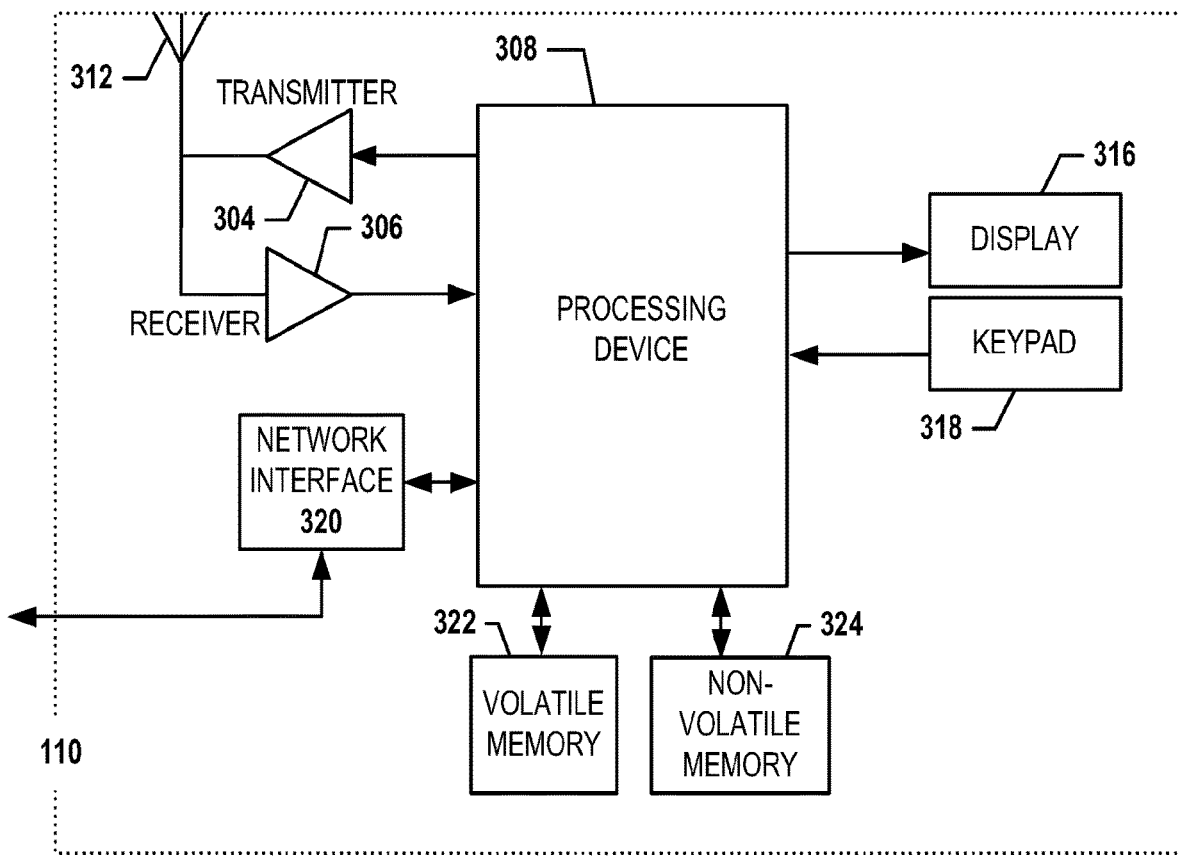

FIG. 3 is an exemplary schematic diagram of a user computing entity according to one embodiment of the present invention.

FIGS. 4A, 4B, and 4C provide three views of the deep learning model at three increasing levels of operational detail from most technical (A) to highest level of operation (C). Panel A illustrates a mortality prediction calculation for an example data segment x of five hours of patient data and corresponding hourly acuity assessments p, where at each time point only the current and previous time steps are used in attention calculations and mortality predictions, in an example embodiment. Panel B displays a more general and compact form for the same stages of data transformation as Panel A. Panel C describes the high-level inputs and outputs of an example embodiment of the deep learning model, where along with overall acuity assessment, interpretable prediction rationale by way of salient sequence patterns are visualized by a heat map of self-attention weights.

Figure 5:
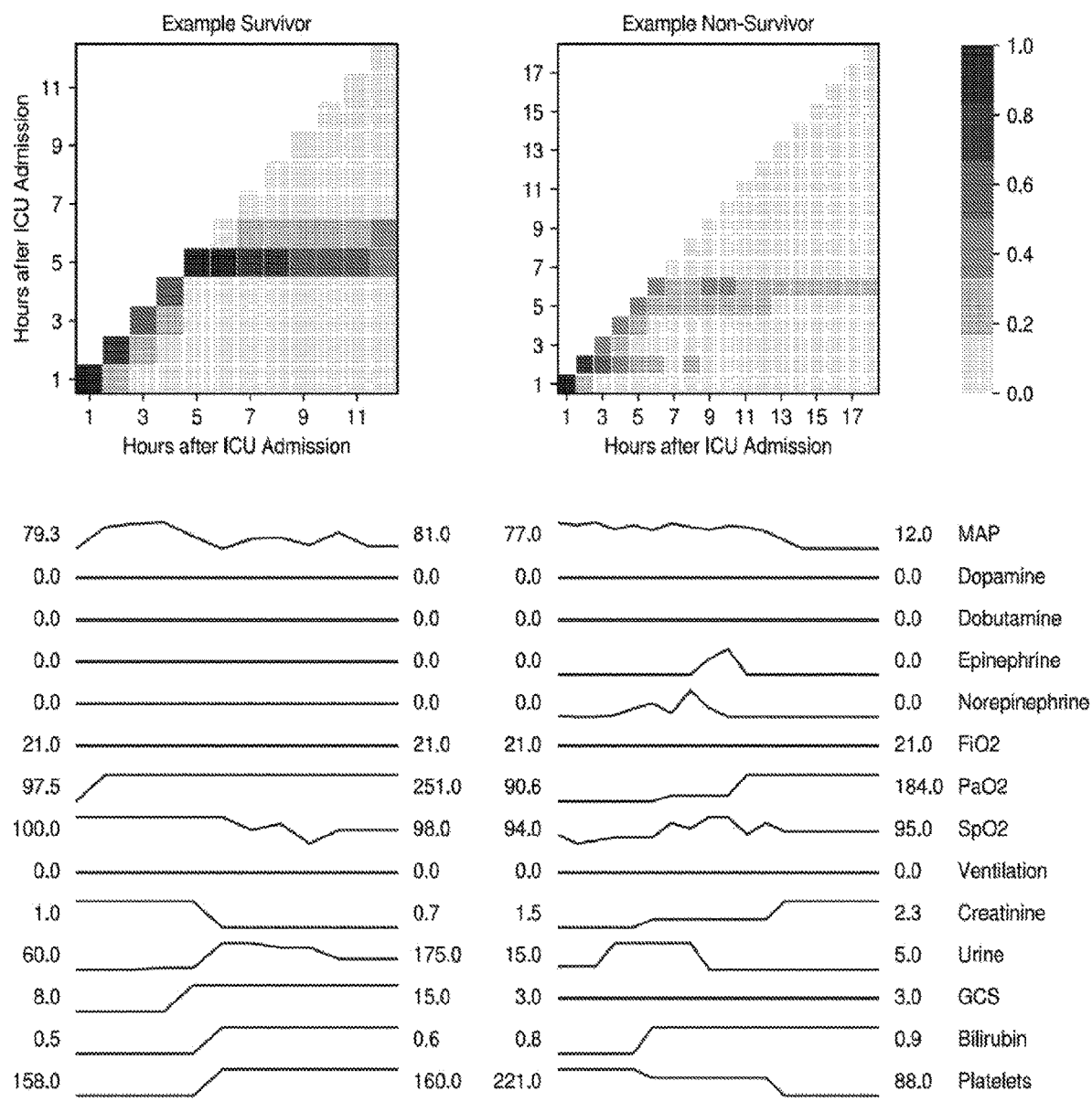

FIG. 5 provides a visualization of self-attention distributions for an example survivor and an example non-survivor, using an example embodiment of the deep learning model. Darker squares indicate increased model focus as a function of the passage of time (x-axis). Shown also are variable time series at each time step (one hour, in this example embodiment) of the ICU stay, with initial and final measurement values shown on the left and right respectively. Some of the shown values correspond to mean arterial pressure (MAP), fraction of inspired oxygen (FiO2), partial pressure of oxygen (SpO2), and Glasgow Coma Scale (GCS).

FIG. 6 provides a table that gives a high-level overview of an example deep learning model (e.g., a DeepSOFA model) and SOFA baseline model operations.

FIG. 7 provides a compact view (left) and an expanded view (right) of an RNN, in accordance with an example embodiment. For simplicity, we omit the fully-connected layer(s) typically placed between hidden state $h_t$ and prediction $y_t$. In this figure, y is taken to be the final prediction of interest for a traditional sequence classification task. However, various embodiments of the deep learning model use all time step predictions $y_t$ for real-time acuity assessment and mortality prediction at each periodic time step (e.g., every hour) following initiation of a patient interaction, admission, and/or the like (e.g., patient ICU admission).

Figure 8:
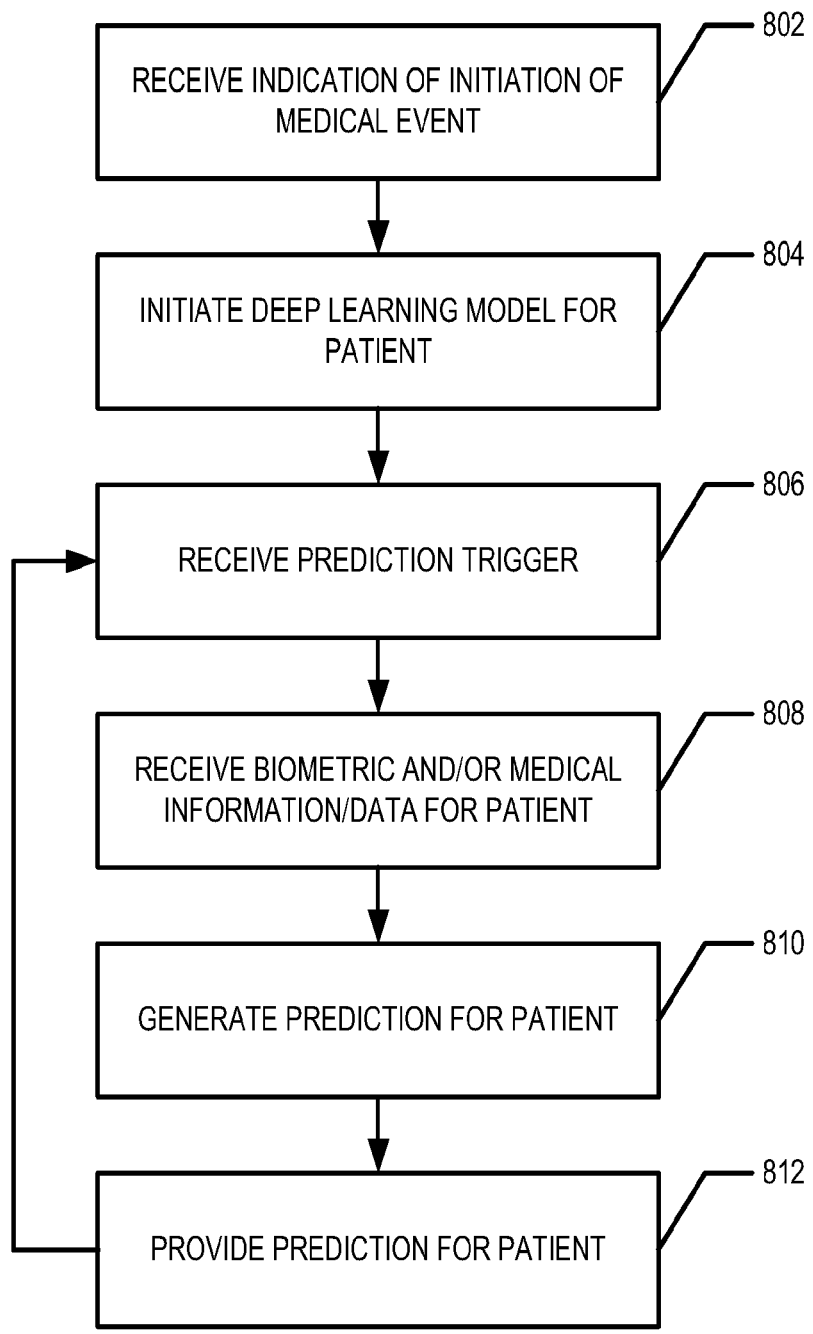

FIG. 8 provides a flowchart illustrating example processes, procedures, and/or operations for using a deep learning model, according to an example embodiment.

DETAILED DESCRIPTION OF SOME EXAMPLE EMBODIMENTS

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout.

The availability of temporal trends and high-fidelity physiologic measurements in the ICU offers the opportunity to apply computational approaches beyond existing conventional models. Example embodiments of the present invention provide an acuity score framework that encompasses the full scope of a patient's physiologic measurements over time to generate dynamic in-hospital mortality predictions. Various embodiments use deep learning, a branch of machine learning that encompasses models and architectures that learn optimal features from the data itself, and capturing increasingly complex representations of raw data by combining layers of nonlinear data transformations'

Deep learning models automatically discover latent patterns and form high-level representations from large amounts of raw data without the need for manual feature extraction based at least in part on a priori domain knowledge or practitioner intuition, which is time-consuming and error-prone. Various embodiments provide a deep learning model, referred to as the DeepSOFA model herein that employs a clinician-interpretable variant of RNN to analyze multivariate temporal clinical data, such as patient data corresponding to a patient in the ICU, for example.

Various embodiments relate to mortality prediction on various time scales (e.g., per hour, per minute, and/or the like). In various embodiments, mortality predictions are determined for patient's undergoing medical procedures, surgical procedures, and/or the like. For example, background information/data captured prior to the medical procedure, surgical procedure, and/or the like may be provided to a first module and/or static information/data module of a deep learning model. In an example embodiment, the background information/data is captured up to one year prior to the medical procedure, surgical procedure, and/or the like. In an example embodiment, at least some of the background information/data is extracted from the patient's electronic health record. A plurality of intraprocedural time series may be provided to a second module or time series module of the deep learning model. For example, the plurality of intraprocedural time series may comprise a plurality of measurements taken spaced apart in time and during the performance of the procedure. The deep learning model may then generate mortality predictions for during the procedure and/or after the procedure.

I. COMPUTER PROGRAM PRODUCTS, METHODS, AND COMPUTING ENTITIES

Embodiments of the present invention may be implemented in various ways, including as computer program products that comprise articles of manufacture. A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

II. EXEMPLARY SYSTEM ARCHITECTURE

FIG. 1 provides an illustration of an exemplary embodiment of the present invention. As shown in FIG. 1, this particular embodiment may include one or more assessment computing entities 100, one or more user computing entities 110, one or more records computing entities 120, one or more sensors 115, and one or more networks 105. Each of these components, entities, devices, systems, and similar words used herein interchangeably may be in direct or indirect communication with, for example, one another over the same or different wired or wireless networks 105. Additionally, while FIG. 1 illustrates the various system entities as separate, standalone entities, the various embodiments are not limited to this particular architecture.

1. Exemplary Assessment Computing Entity

FIG. 2 provides a schematic of an assessment computing entity 100 according to one embodiment of the present invention. An assessment computing entity 100 may belong to, a medical facility, hospital, clinic, diagnostic service, healthcare provider, healthcare provider group, and/or the like. However, the assessment computing entity 100 may belong a third party computing service that performs remote computations for a medical facility. In an example embodiment, an assessment computing entity 100 may be configured to receive medical information/data from one or more sensors 115, one or more user computing entities 110, and/or one or more record computing entities 120. In an example embodiment, the assessment computing entity 100 is configured to execute a deep learning model (e.g., a DeepSOFA model, in an example embodiment). In an example embodiment, an assessment computing entity 100 may be configured to store and/or provide one or more control one or more acuity scores to one or more user computing entities 110, and/or one or more record computing entities 120.

In general, the terms computing entity, computer, entity, device, system, and/or similar words used herein interchangeably may refer to, for example, one or more computers, computing entities, desktop computers, mobile phones, tablets, phablets, notebooks, laptops, distributed systems, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the assessment computing entity 100 may also include one or more communications interfaces 220 for communicating with various computing entities, such as by communicating data, content, information, and/or similar terms used herein interchangeably that can be transmitted, received, operated on, processed, displayed, stored, and/or the like. For instance, the assessment computing entity 100 may communicate with user computing entities 110, records computing entity 120, and/or a variety of other computing entities.

As shown in FIG. 2, in one embodiment, the assessment computing entity 100 may include or be in communication with one or more processing elements 205 (also referred to as processors, processing circuitry, and/or similar terms used herein interchangeably) that communicate with other elements within the assessment computing entity 100 via a bus, for example. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the assessment computing entity 100 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity—relationship model, object model, document model, semantic model, graph model, and/or the like.

In one embodiment, the assessment computing entity 100 may further include or be in communication with volatile media (also referred to as volatile storage, memory, memory storage, memory circuitry and/or similar terms used herein interchangeably). In one embodiment, the volatile storage or memory may also include one or more volatile storage or memory media 215, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the assessment computing entity 100 with the assistance of the processing element 205 and operating system.

As indicated, in one embodiment, the assessment computing entity 100 may also include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the assessment computing entity 100 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra wideband (UWB), infrared (IR) protocols, near field communication (NFC) protocols, Wibree, Bluetooth protocols, wireless universal serial bus (USB) protocols, and/or any other wireless protocol.

Although not shown, the assessment computing entity 100 may include or be in communication with one or more input elements, such as a keyboard input, a mouse input, a touch screen/display input, motion input, movement input, audio input, pointing device input, joystick input, keypad input, and/or the like. The assessment computing entity 100 may also include or be in communication with one or more output elements (not shown), such as audio output, video output, screen/display output, motion output, movement output, and/or the like.

In various embodiments, the assessment computing entity 100 may further comprise a user interface for user interaction. In various embodiments, the user interface may comprise one or more input devices (e.g., soft or hard keyboard, joystick, mouse, touch screen device, microphone, and/or the like) for receiving user input and one or more output devices (e.g., speakers, display, and/or the like) for providing output to a user.

As will be appreciated, one or more of the assessment computing entity's 100 components may be located remotely from other assessment computing entity 100 components, such as in a distributed system. Furthermore, one or more of the components may be combined and additional components performing functions described herein may be included in the assessment computing entity 100. Thus, the assessment computing entity 100 can be adapted to accommodate a variety of needs and circumstances. As will be recognized, these architectures and descriptions are provided for exemplary purposes only and are not limiting to the various embodiments.

2. Exemplary User Computing Entity

A user may be an individual, a family, a company, an organization, an entity, a department within an organization, a representative of an organization and/or person, and/or the like. In one example, users may be medical personnel, doctors, physician assistants, nurses, patients, and/or the like. For instance, a user may operate a user computing entity 110 that includes one or more components that are functionally similar to those of the assessment computing entity 100. FIG. 3 provides an illustrative schematic representative of a user computing entity 110 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, wearables, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. User computing entities 110 can be operated by various parties. As shown in FIG. 3, the user computing entity 110 can include an antenna 312, a transmitter 304 (e.g., radio), a receiver 306 (e.g., radio), and a processing device 308 (e.g., CPLDs, microprocessors, multi-core processors, coprocessing entities, ASIPs, microcontrollers, and/or controllers) that provides signals to and receives signals from the transmitter 304 and receiver 306, respectively.

The signals provided to and received from the transmitter 304 and the receiver 306, respectively, may include signaling information in accordance with air interface standards of applicable wireless systems. In this regard, the user computing entity 110 may be capable of operating with one or more air interface standards, communication protocols, modulation types, and access types. More particularly, the user computing entity 110 may operate in accordance with any of a number of wireless communication standards and protocols, such as those described above with regard to the assessment computing entity 100. In a particular embodiment, the user computing entity 110 may operate in accordance with multiple wireless communication standards and protocols, such as UMTS, CDMA2000, 1×RTT, WCDMA, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the user computing entity 110 may operate in accordance with multiple wired communication standards and protocols, such as those described above with regard to the assessment computing entity 100 via a network interface 320.

Via these communication standards and protocols, the user computing entity 110 can communicate with various other entities using concepts such as Unstructured Supplementary Service Data (US SD), Short Message Service (SMS), Multimedia Messaging Service (MMS), Dual-Tone Multi-Frequency Signaling (DTMF), and/or Subscriber Identity Module Dialer (SIM dialer). The user computing entity 110 can also download changes, add-ons, and updates, for instance, to its firmware, software (e.g., including executable instructions, applications, program modules), and operating system.

According to one embodiment, the user computing entity 110 may include location determining aspects, devices, modules, functionalities, and/or similar words used herein interchangeably. For example, the user computing entity 110 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites. The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. Alternatively, the location information can be determined by triangulating the user computing entity's 110 position in connection with a variety of other systems, including cellular towers, Wi-Fi access points, and/or the like. Similarly, the user computing entity 110 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The user computing entity 110 may also comprise a user interface (that can include a display 316 coupled to a processing device 308) and/or a user input interface (coupled to a processing device 308). For example, the user interface may be a user application, browser, user interface, and/or similar words used herein interchangeably executing on and/or accessible via the user computing entity 110 to interact with and/or cause display of information from the assessment computing entity 100, as described herein. The user input interface can comprise any of a number of devices or interfaces allowing the user computing entity 110 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the user computing entity 110 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The user computing entity 110 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the user computing entity 110. As indicated, this may include a user application that is resident on the entity or accessible through a browser or other user interface for communicating with the assessment computing entity 100 and/or various other computing entities.

In another embodiment, the user computing entity 110 may include one or more components or functionality that are the same or similar to those of the assessment computing entity 100, as described in greater detail above. As will be recognized, these architectures and descriptions are provided for exemplary purposes only and are not limiting to the various embodiments.

3. Exemplary Sensors

In various embodiments, one or more sensors 115 may be configured to capture information/data corresponding to a patient. For example, a sensor 115 may capture biometric information/data, medical information/data, and/or the like. For example, the one or more sensors 115 may include a heart monitor, a blood pressure monitor, a blood oxygen monitor, a blood sugar monitor, and/or other sensor configured to capture biometric and/or medical information/data regarding a patient. In an example embodiment, a sensor 115 is in communication with a records computing entity 120 and/or user computing entity 110. For example, the sensor 115 may comprise one or more biometric and/or medical information/data capturing elements, a processing element configured to process signals generated by the one or more biometric and/or medical information/data, and a communication interface configured to enable the sensor 115 to communicate with a records computing entity 120 and/or user computing entity 110 (e.g., via network 105). For example, a sensor 115 may transmit one or more instances of biometric and/or medical information/data corresponding to a patient to a user computing entity 110 corresponding to a medical personnel on the patient's care team or to a records computing entity 120 for inclusion of the one or more instances of biometric and/or medical information/data in a digital health record corresponding to the patient, and/or the like.

4. Exemplary Records Computing Entity

A records computing entity 120 may belong to, a medical facility, hospital, clinic, diagnostic service, healthcare provider, healthcare provider group, and/or the like. However, the assessment computing entity 120 may belong a third party service that remotely and securely stores patient health records for a medical facility. In an example embodiment, a records computing entity 120 may be configured to receive biometric and/or medical information/data from one or more sensors 115 and/or one or more user computing entities 110 and receive one or more acuity scores from one or more assessment computing entities 100 and store the biometric and/or medical information/data and/or acuity score in a digital health record corresponding to the patient. In an example embodiment, a records computing entity 120 may be configured to provide biometric and/or medical information/data corresponding to a patient to an assessment computing entity 100 such that the assessment computing entity 100 may generate and/or determine an acuity score for a patient. In various embodiments, a records computing entity 120 includes one or more components that are functionally similar to those of the assessment computing entity 100. For example, in an example embodiment, a records computing entity 120 includes a processing element, volatile memory, non-volatile memory, a communications interface, and optionally includes a user interface. In an example embodiment, an assessment computing entity 100 is a module of a records computing entity 120.

III. EXEMPLARY SYSTEM OPERATION

According to various embodiments, the assessment computing entity 100 may be configured to determine an acuity score and/or mortality prediction for one or more patients. In an example embodiment, the one or more patients are critically ill and/or injured and have been emitted to an ICU. In an example embodiment, the one or more patients are planned to undergo, are undergoing, and/or have undergone a medical procedure, surgical procedure, and/or the like. The assessment computing entity 100 may receive biometric and/or medical information/data corresponding to the patient from one or more user computing entities 110, one or more sensors 115, and/or one or more records computing entities 120. In an example embodiment, the assessment computing entity 100 may receive and/or access static information/data corresponding to the patient (e.g., background information/data) taken up to a year prior to the current medical event (e.g., ICU emission, surgical procedure, and/or the like). For example, the static and/or background information/data may be extracted from the patient's electronic health record, in an example embodiment. The assessment computing entity 100 may further receive time series information/data corresponding to biometric and/or medical information/data corresponding to the current medical event. The assessment computing entity 100 may generate, determine, and/or compute an acuity score for a patient in response to receiving an acuity score request, periodically (e.g., every minute, every ten minutes, once per half hour, once per hour, and/or the like), after a time period that was determined based at least in part on one or more of the patient's previous acuity scores, upon certain criteria and/or milestones being met (e.g., the patient being emitted to the ICU, anesthesia or other medication being administered to the patient, the patient coding, patient being removed from a breathing assistance apparatus, and/or the like), and/or the like.

Figure 4:
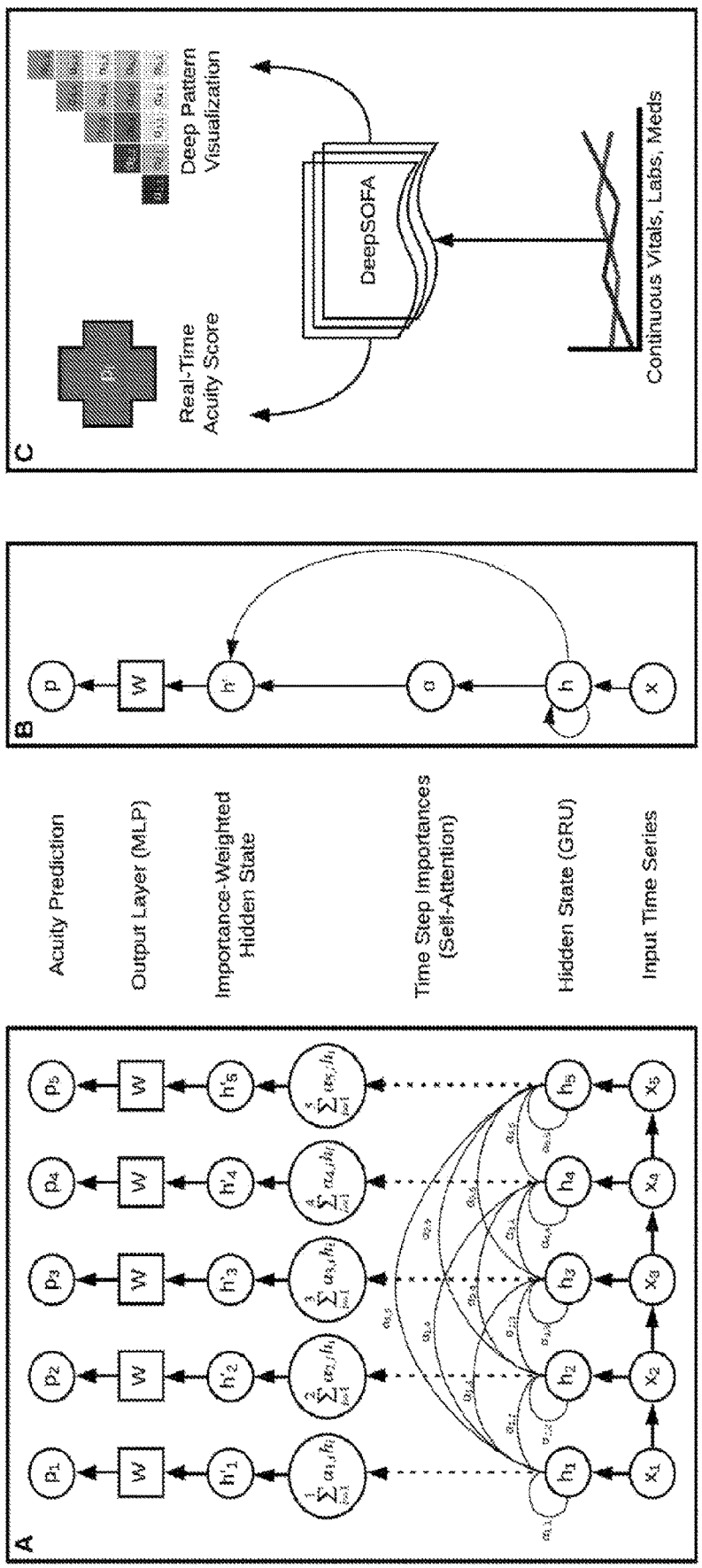

In various embodiments, the mortality prediction and/or acuity score is determined using a deep learning model. In an example embodiment, the deep learning model is and/or comprises a modified RNN with GRU, a deep learning model ideal for working with sequentially ordered temporal data. An example deep learning model described herein is referred to as a DeepSOFA model. FIG. 4 shows a high-level overview of the DeepSOFA model at three various levels of operational detail. In an example embodiment, the RNN of the DeepSOFA model internally and continuously updates its parameters based at least in part on multivariate inputs from both the current time step and one or more previous time steps. As such, a mortality prediction incorporates patterns detected across the entirety of a set of patient information/data corresponding to a patient interaction, admission, and/or the like (e.g., corresponding to a patient ICU stay, for example), with recognition of longer-range temporal relationships aided by the addition of GRUs of the DeepSOFA model.

One of the weaknesses of deep learning techniques is the inherent difficulty in understanding the relative importance of model inputs in generating the output. In the case of mortality prediction, clinicians are interested not only in the likelihood of death, but also in knowing which factors are primarily responsible for the risk of death. If such factors are modifiable, then they represent therapeutic targets. If such factors are not modifiable, then the sustained provision of life-prolonging interventions may reach futility. To improve clinical interpretability, various embodiments of the Deep-SOFA model comprise a modified GRU-RNN network that includes a final self-attention mechanism to allow clinicians to understand why the DeepSOFA model is making its predictions. At each time step (e.g., each hour during a real-time ICU stay, in an example embodiment), the self-attention mechanism focuses on salient deep representations of all previous time points, assigning relevance scores to every preceding time step that determine the magnitude of each time step's contribution to the DeepSOFA model's overall mortality prediction. Subject to the constraint that each time step's relevance scores must sum to 1, we are able to see exactly which time steps of the multivariate time series the DeepSOFA model thinks are most important, and how sudden the shift in attention happens. An example of this interpretable attention mechanism is shown in FIG. 5 where along with a mapping back to the original input time series, the DeepSOFA model is able to justify its mortality predictions by changes in each of the input variables.

DeepSOFA mortality predictions were compared with two baseline models using traditional SOFA scores, which were calculated at each hour using the previous 24 hours of electronic health record (EHR) data. The mortality predictions associated with calculated SOFA scores were derived from both published mortality rate correlations with any given score, which we refer to as "Bedside SOFA", and to overall area under the curve (AUC) derived from raw SOFA scores, which we refer to as "Traditional SOFA". At any time step during an ICU admission, the Bedside SOFA baseline model associated the current SOFA score with a predicted probability of mortality, as would be performed using an online calculator, in which total SOFA scores correlate with mortality ranges. The Traditional SOFA model is based at least in part on retrospective analysis that derives AUC from raw SOFA scores and outcomes, and while not suitable for real-time prediction in practice, is a reasonable and contemporary baseline and an appropriate challenger to compare with the DeepSOFA model. A high-level comparison between the prediction and AUC calculation for all three models used in our experiments can be found in FIG. 6.

Our baselines are based at least in part on both current practice (Bedside SOFA) and recent retrospective methods (Traditional SOFA). Both of these baselines utilize a single feature (current SOFA score) from patient time series for making hourly predictions. As a sensitivity analysis, we also trained two additional conventional machine learning models (logistic regression, random forest) using 84 aggregate features recalculated at every hour after ICU admission, including the following for each of the 14 SOFA variables: minimum value, maximum value, mean value, standard deviation, first value, and last value. The SOFA baselines included in our study outperformed these additional machine learning models.

Though referred to as a DeepSOFA model herein, it should be understood that the model may take as input various medical and/or biometric information/data in addition to and/or instead of the traditional SOFA variables, in various embodiments.

1. Exemplary Deep Learning Model

A. Exemplary Recurrent Neural Network (RNN)

For making acuity assessments and mortality predictions, an example embodiment of the deep learning model utilizes an RNN, a type of deep learning algorithm that is naturally suited for processing sequential data. In various embodiments, the deep learning model is configured to make acuity assessments and/or mortality predictions on a periodic (e.g., each minute, hourly, and/or the like as appropriate for the medical event) and/or triggered basis. The key attribute of an RNN which makes it especially useful for modeling temporal data is its notion of internal memory; as each new time step t of a sequence is processed, an RNN updates its hidden state $h_t$ by combining the current step's data with the deep representation of all data it has seen in the past. In its simplest form, the calculation of the RNN internal state is shown in Equation S1, where $U \in \mathbb{R}^{k \times d}$ is the input weight matrix, $V \in \mathbb{R}^{k \times k}$ is the recurrent weight matrix, d is the number of features in the input sequence, k is the tunable dimensionality of the RNN's hidden state, and bias terms are omitted for simplicity.

$$h_t = \sigma(Ux_t + Vh_{t-1}) \tag{S1}$$

At each time step t, the corresponding slice of the input sequence $x_t \in \mathbb{R}^d$ is combined with the previous time step's hidden state $h_{t-1} \in \mathbb{R}^k$ via U, V, and a nonlinear activation function σ such as tan h. In an example embodiment, $h_0$ is often initialized to a vector of zeros. In various embodiments, the RNN's weights are trained via backpropagation, a technique for updating a model's internal weights by attributing the final model error to individual parameters based at least in part on the flow of gradients from a differentiable loss function.

At any point during processing a sequence, the RNN's current hidden state $h_t$ is the representation of the entire sequence up to the current time. Once the sequence has been fully passed through the RNN, the final hidden state is taken as the deep representation of the entire sequence, which can then be passed to subsequent layers for tasks such as classification. FIG. 7 shows two perspectives of an example RNN, in accordance with various embodiments.

For predicting a classification target (such as the deep learning model's in-hospital mortality) at a given time t, one would pass the RNN's current hidden state through a final classification layer as in Equation S2, where $W_y \in \mathbb{R}^{M \times k}$ is the output weight matrix, M is the number of available prediction classes, k is the tunable dimensionality of the RNN's hidden state, $h_t$ is the RNN's internal hidden state at time t, and the bias term is omitted for simplicity. In an example embodiment, M is equal to two, as the deep learning model's prediction has two available prediction classes (e.g., survivor and non-survivor).

$$y_t = W_y h_t \tag{S2}$$

B. Gated Recurrent Units (GRU)

In the previous section, we described the simplest form of a recurrent neural network. In practice, these standard RNNs suffer from what is known as the exploding gradient problem, in which repeated multiplications and nonlinear activations involved in updating the hidden state over time result in unstable chain rule-based gradient calculations during the backpropagation process. This issue, combined with the simple form of an RNN's internal memory, often results in non-robust models that are incapable of dealing with longer sequences and at best fail to utilize patterns or dependencies from distant past time steps.

In practice, two popular RNN modifications are commonly used, and both attempt to solve the issues above using slightly different techniques. The first RNN variant to be widely adopted is known as long short-term memory (LSTM), which augments the traditional RNN with additional weight matrices and gating functions to improve long-range sequential processing. More recently, GRUs have gained in popularity as a comparable alternative to the LSTM, again involving the introduction of new weights and operations for internally processing a sequence. Various embodiments of the deep learning model use GRU networks, with the advantage that the GRU networks include fewer required parameters than LSTM networks. An example embodiment of the deep learning model uses an LSTM network. Equations S3-S6 illustrate the modifications to the traditional RNN from Equation S1, including the introduction of a "reset gate" $r_t$, an "update gate" $z_t$, and use of the elementwise multiplication operation $\odot$. Bias terms are omitted for simplicity.

$$r_t = \sigma(W_r x_t + U_r h_{t-1}) \tag{S3}$$

$$z_t = \sigma(W_z x_t + U_z h_{t-1}) \tag{S4}$$

$$h'_t = \Phi(W_x x_t + r_t \odot (Uh_{t-1})) \tag{S5}$$

$$h_t = (1 - z_t) h_{t-1} + z_t h'_t \tag{S6}$$

In essence, the introduction of gating mechanisms allows the RNN to become more discretionary in the information it learns and remembers, and the modifications expand the capacity of its internal memory to incorporate important data from potentially long-distant time steps.

C. Exemplary Self-Attention Mechanism

At each time step during a patient interaction, admission, and/or the like (e.g., at each hour during a patient ICU stay, each minute during a medical/surgical procedure), the deep learning model (e.g., operating on the assessment computing entity 100) makes a mortality probability calculation based at least in part on the sequence of biometric and/or medical information/data corresponding to the patient available through the current time step. In an example embodiment, the biometric and/or medical information/data comprises a sequence of EHR measurements. In various embodiments, the assessment computing entity 100 receives the biometric and/or medical information/data from one or more of one or more user computing entities 110, one or more sensors 115, or one or more records computing entities 120. The simplest option for a given time step would involve passing the GRU's current hidden state h, through a final output classification layer (See Equation S2) to produce the probability of in-hospital mortality given the sequence of measurements encountered thus far (e.g., $(x_1, \ldots, x_t)$. This approach for temporal classification assumes that at a given time, the entirety of information contained in the input sequence up through that time can be fully represented by the fixed-dimensional vector $h_t$.

Rather than relying on the most recent hidden state of the GRU for making a prediction, various embodiments of the deep learning model instead provide a weighted average of all prior hidden states to the final classification layer. The advantages to this approach are twofold. First, the sequence in effect becomes more distilled, by dampening inconsequential time steps and amplifying important ones relative to the final outcome. Second, these scalar time step weights can be used for providing clinician insight into the internal reasoning of the GRU's predictions, since larger time step weights directly influences the averaged hidden state used for prediction and can thus be interpreted as denoting important time steps relative to the outcome of interest.

In the deep learning community, the process of learning scalar time step values to weight a sequence for saliency falls under the umbrella category of an attention mechanism, named as such in reference to the act of a model "focusing" on particular pieces of an input rather than its entirety. In general, a self-attention mechanism allows the inputs to interact with each other ("self") and find out who they should pay more attention to ("attention"). The outputs are aggregates of these interactions and attention scores.

In various embodiments, the deep learning model uses the constraint that all attention weights for a given sequence sum to 1 via use of a softmax function over the time dimension, thus encouraging larger weights being placed on the most important time steps of input data. Equations S7 and S8 illustrate an attention mechanism, used in an example embodiment, involving a global attention vector $W_{att} \in \mathbb{R}^{1 \times k}$ where relative importance (known in literature as compatibility) of each time step's hidden state $h_i \in \mathbb{R}^{k \times 1}$ is calculated via dot product with the global attention vector, and a softmax function over compatibility scores is applied to yield a scalar weight $\alpha_i$ for each time step $I=1, 2, \ldots, t$, where the new sequence representation at a given time is computed as a weighted sum of all preceding hidden states.

$$\alpha_i = \text{softmax}(W_{att} h_i) \quad (S7)$$

$$h_t = \Sigma_{i=0}^{t} \alpha_i h_i \quad (S8)$$

In various embodiments, the deep learning model directly calculates time step compatibilities between hidden time steps themselves, rather than learning a global attention vector as in Equation S7. Since the deep learning model is centered on patient monitoring (e.g., real-time ICU patient monitoring), at each time step t during a medical event, patient interaction, admission, and/or the like (e.g., a patient's ICU stay, medical/surgical procedure, and/or the like) this self-attention mechanism provides (e.g., to a clinician operating a user computing entity 110) with information regarding which prior time steps were most influential in generating the current representation $h_t$ and current prediction $y_t$. Thus, in various embodiments, the self-attention features of the deep learning model enable clinicians to understand the interactions between changes in patient biometric and/or medical information/data in real-time. Equations S9 and S10 describe attention process implemented in an example embodiment of the deep learning model, where weight matrices $W_Q \in \mathbb{R}^{k \times k}$, $W_K \in \mathbb{R}^{k \times k}$ and $W_V \in \mathbb{R}^{k \times k}$ are learned projections of the same hidden representation $h_t \in \mathbb{R}^{k \times 1}$.

$$\alpha_i = \text{softmax}(W_Q h_i \cdot W_K h_i) \quad (S9)$$

$$h_t = \Sigma_{i=0}^{t} \alpha_i W_V h_i \quad (S10)$$

At each time step t during a medical event, patient interaction, admission, and/or the like (e.g., a patient's ICU stay, a medical/surgical procedure), attention values $\alpha_i \forall i=1, \ldots, t$ are recalculated to present a current, updated view on the most important time steps influencing the mortality prediction provided by the deep learning model. Thus, various embodiments of the deep learning model a framework to consider real-time self-attention distributions that are updated on-the-fly and only consider currently available patient biometric and/or medical information/data for immediate clinician interpretability.

D. Exemplary Model Training

In various embodiments, the deep learning model (e.g., a DeepSOFA model, in an example embodiment) comprises (1) an input layer, (2) a single GRU layer, (3) a self-attention layer, (4) a dropout layer, and (5) a final fully-connected output layer for classification. In an example embodiment, the deep learning model consists of (1) an input layer, (2) a single GRU layer, (3) a self-attention layer, (4) a dropout layer, and (5) a final fully-connected output layer for classification. As an example embodiment, the deep learning model is focused on real-time prediction, the final mortality target is replicated across all input time steps to encourage a correct prediction as early as possible, in the example embodiment. Various embodiments of the deep learning model are trained to optimize cross-entropy loss averaged across all time steps of a patient interaction, admission, and/or the like (e.g., a patient ICU stay) (Equation S11), where $W_Y$ is the output weight matrix of the final classification layer, $h_t$ is the attention-weighted sum of available hidden states at each hour t $\forall t=1, \ldots, T$, and T is the number of time steps (e.g., minutes, hours) the medical event, patient interaction, admission, and/or the like lasted (e.g., the number of time steps for which the patient was in the ICU, the number of time steps since initiation of a medical/surgical procedure, and/or the like). Since we apply target replication, y is the same for all time steps t for a given patient interaction, admission, and/or the like (e.g., patient ICU stay).

$$\text{loss} = \frac{1}{T} \sum_{t=0}^{T} -[y * \log(W_Y h_t) + (1-y)\log(1 - W_Y h_t)] \quad (S11)$$

Model training was terminated when the AUC on the validation set did not increase for 5 epochs, in an example embodiment. Various embodiments of the deep learning model were specifically trained with a focus on real-time implementation; thus, during training we implemented the dynamic, time step self-attention updates by copying the input sequence of length T to a T×T matrix and applying a lower triangular mask for preventing the model from looking ahead to time steps occurring in the future.

E. Exemplary Model Parameters

An example embodiment, the deep learning model uses a GRU layer with 64 hidden units, 20% dropout, L2 weight regularization of 1e-6, a batch size of 16, and an Adam optimizer.

2. Exemplary Use of a Deep Learning Model

FIG. 8 provides a flowchart illustrating example processes, procedures, and/or operations for using a deep learning model in an example embodiment. In various embodiments, the deep learning model has been previously trained. At step/operation 802, an assessment computing entity 100 receives an indication that a patient interaction, admission, medical event, and/or the like has been initiated. For example, the assessment computing entity 100 may receive (e.g., via communications interface 220) an indication provided by a user computing entity 110 and/or a records computing entity 120 that a patient interaction, admission, and/or the like has been initiated. In an example embodiment, the initiation of the patient interaction, admission, and/or the like is the admission of the patient to the ICU. For example, the medical event could be an ICU stay. In various embodiments, the initiation of the patient interaction, admission, and/or the like is the planning/scheduling of a medical/surgical procedure, a patient reporting for a medical/surgical procedure, initiation of a medical/surgical procedure, and/or the like. For example, the medical event could be a medical/surgical procedure. In an example embodiment, a clinician (e.g., nurse, doctor, technician, and/or other healthcare worker) may operate a user computing entity 110 (e.g., via the user interface) to provide information/data indicating that the patient interaction, admission, and/or the like has been initiated. In an example embodiment, the user computing entity 110 provides (e.g., transmits) an indication of the initiation of the patient interaction, admission, and/or the like to a records computing entity 120 for inclusion in the patients EHR. In an example embodiment, the user computing entity 110 may further provide information/data associating one or more sensors 115 to the patient. In an example embodiment, responsive to receiving the indication of the initiation of the patient interaction, admission, and/or the like, the records computing entity 120 may update the patient's EHR accordingly and generate and provide (e.g., transmit) a request for an acuity score and/or mortality prediction such that the assessment computing entity 100 receives the request. In an example embodiment, the user computing entity 110 may generate and provide (e.g., transmit) a request for an acuity score and/or mortality prediction such that the assessment computing entity 100 receives the request. Thus, the assessment computing entity 100 may receive an indication of the initiation of the patient interaction, admission, and/or the like, possibly in the form of a request for an acuity score and/or mortality prediction.

At step/operation 804, a deep learning model (e.g., a DeepSOFA model, in an example embodiment) is initiated for the patient. For example, the assessment computing entity 100 may initiate a deep learning model for the patient. In an example embodiment, to initiate the deep learning model, the assessment computing entity 100 may access (e.g., request and receive) information/data from the patient's EHR, such as biometric and/or medical information/data, patient history information/data, and/or the like. In an example embodiment, this accessed information/data may then be used for initial time step information/data for the time series used by the deep learning model to generate predictions.

At step/operation 806, a prediction trigger is received, determined, and/or identified. For example, the assessment computing entity 100 may receive, determined, and/or identify a prediction trigger. For example, a user computing entity 110 and/or records computing entity 120 may generate and provide (e.g., transmit) a request for an acuity score and/or mortality prediction such that the assessment computing entity 100 receives the request and the request is subsequently identified as a prediction trigger. In an example embodiment, the assessment computing entity 100 is configured to periodically (e.g., every minutes, every five minutes, every fifteen minutes, every half hour, every hour, and/or the like as appropriate for the medical event) generate an acuity score and/or mortality prediction for the patient. In such an example embodiment, when the assessment computing entity 100 determines that a time period corresponding to the periodicity with which acuity scores and/or mortality predictions are to be generated has passed, the assessment computing entity 100 may identify a prediction trigger. In an example embodiment, the periodicity with which acuity scores and/or mortality predictions are to be generated is a predetermined time period (e.g., every half hour, every hour, and/or the like) or a configurable time period that is determined based at least in part on one or more previous acuity scores and/or mortality predictions for the patient.

At step/operation 808, biometric and/or medical information/data for the patient is received. For example, the assessment computing entity 100 may receive (e.g., via the communications interface 220) biometric and/or medical information/data for the patient. In an example embodiment, the biometric and/or medical information/data is received from one or more user computing entities 110, one or more sensors 115, and/or one or more records computing entities 120. For example, biometric and/or medical information/data may be captured during the medical event (e.g., via one or more sensors 115) and provided to the assessment computing entity 100. For example, the biometric and/or medical information/data may be information/data corresponding to the patient during the most recent time step (e.g., $x_t$). For example, the biometric and/or medical information/data may comprise information/data corresponding to a particular time step for one or more time series of information/data used to generate the prediction. In an example embodiment, the biometric and/or medical information/data is received with the prediction trigger and/or is requested in response to the prediction trigger.

At step/operation 810, a prediction for the patient is generated. For example, the assessment computing entity 100 generates a prediction for the patient. In an example embodiment, the prediction may comprise an acuity score, a mortality prediction, one or more self-attention parameters and/or distributions, and/or the like. For example, the deep learning model corresponding to the patient may be updated based at least in part on the biometric and/or medical information/data corresponding to the patient for the most recent time step (e.g., using Equations S1, S3-S6, and/or the like). For example, the hidden states of the deep learning model corresponding to the patient may be updated based at least in part on the biometric and/or medical information/data corresponding to the most recent time step. The updated deep learning model may then be used to generate the prediction (e.g., using Equations 2, 7-10, and/or the like). For example, the output layer of the deep learning model may be used to generate the prediction based at least in part on the updated hidden states of the deep learning model.

At step/operation 812, the prediction for the patient is provided. For example, the assessment computing entity 100 provides (e.g., transmits) the prediction for the patient such that one or more records computing entities 120 receive the prediction and the records computing entities 120 will update the patient's EHR based at least in part on the prediction, in an example embodiment. For example, the assessment computing entity 100 provides (e.g., transmits) the prediction for the patient such that one or more user computing entities 110 receive the prediction and the user computing entities 110 will process the prediction and provide (e.g., via a user interface such as display 316) at least a portion of the prediction such that a user (e.g., clinician, patient, and/or the like) may review the at least a portion of the prediction. As noted above, the prediction may comprise an acuity score, mortality prediction, one or more self-attention parameters and/or distributions, and/or the like. In an example embodiment, the acuity score, mortality prediction, one or more self-attention parameters and/or distributions and/or the like is provided for user review in (near) real-time (e.g., with respect to the biometric and/or medical information/data for the more recent time step). In an example embodiment, the one or more self-attention parameter and/or distributions may indicate and/or flag which parameters represent therapeutic targets such that the acuity score and/or mortality prediction may be improved effectively through clinical therapies targeting such therapeutic targets. The process may then return to step/operation 806 when another prediction trigger is received, determined, and/or identified and the cycle may continue for the remainder of the patient interaction, admission, medical event, and/or the like (e.g., the patient's ICU stay, medical/surgical procedure, and/or the like).

3. Exemplary Combined Static and Time Series Model

In various embodiments, a combined static and time series deep learning model is provided. For example, the model may be configured to receive static and/or background information/data corresponding to a patient that was captured prior to the current medical event (e.g., ICU admission, medical/surgical procedure, and/or the like). The model may be further configured to receive time series information/data (e.g., time series of measurements) corresponding to the patient that is captured during the current medical event. For example, the model may comprise a first or static module configured to receive and process the static and/or background information/data and a second or time series module configured to receive and process time series data corresponding to the current medical event, as described above with respect to the deep learning model.

For example, the static and/or background information/data may be captured up to a year prior to the current medical event, in an example embodiment. For example, the static and/or background information/data may comprise a plurality of clinical descriptors of health. In various embodiments, the static and/or background information/data may comprise demographic and/or socioeconomic indicators; planned procedure and/or provider information; admission diagnoses; Charlson comorbidities; summary statistics of select medications, laboratory tests, physiological measurements, and/or the like; and/or other information/data corresponding to the patient's health. In an example embodiment, raw the time series of measurements captured during the medical event include a plurality of measurements comprising one or more of systolic blood pressure, diastolic blood pressure, mean arterial pressure (MAP), end-tidal carbon dioxide (EtCO2), fraction of inspired oxygen (FiO2), heart rate, minimum alveolar concentration (MAC), oxygen flow rate, positive end-expiratory pressure (PEEP), peak inspiratory pressure (PIP), respiratory rate, blood oxygen saturation (SpO2), temperature, urine output, and blood loss. For example, step/operation 804 may comprise accessing (e.g., requesting and receiving) static and/or background information/data, processing of static and/or background information/data (e.g., via the static module of the deep learning model), and/or the like.

For example, at the start of and/or prior to the start of a medical event (e.g., ICU admission, medical/surgical procedure, and/or the like) static and/or background information/data may be extracted from a patient's electronic health record. For example, the initiation of the patient interaction may be the scheduling of a medical event (e.g., medical/surgical procedure), when a patient checks in for a medical event (e.g., medical/surgical procedure), the beginning of a medical event (e.g., when the patient is set up with an IV in preparation for a surgical procedure, for example), and/or the like. During the medical event, measurements are made periodically to generate the time series of measurements and the time series of measurements are provided to the model (e.g., the second and/or time series module of the model) as they are collected. The model may then generate acuity and/or mortality predictions for the patient. In an example embodiment, the time series measurements are captured every minute, every two minutes, every five minutes, every fifteen minutes, every thirty minutes, every hour, and/or the like, as appropriate for the medical event. In various embodiments, the acuity and/or mortality predictions correspond to during the medical event and/or for a period of time after completion of the medical event (e.g., after the completion of a surgical procedure, after discharge from the ICU, and/or the like).

An example embodiment of the combined static and time series model was evaluated by several performance metrics. The example embodiment of the combined static and time series model was compared with a baseline random forest classifier trained on the same input data. 95% confidence intervals were obtained using a bootstrapping procedure with 1000 iterations. The example embodiment of the combined static and time series model showed significant improvements over the baseline random forest classifier in the performance metrics of area under the receiver operation characteristic curve (AUROC) (0.91, with a 95% confidence interval of 0.90-0.93 versus 0.79 with a 95% confidence interval of 0.76-0.81) and area under the precision-recall curve (AUPRC) (0.25 with a 95% confidence interval of 0.21-0.30 versus 0.11 with a 95% confidence interval of 0.09-0.14). The example embodiment of the combined static and time series model performed at least as well as the baseline random forest classifier in the performance metrics of sensitivity (0.90 with a 95% confidence interval of 0.78-0.94 versus 0.79 with a 95% confidence interval of 0.60-0.83), specificity (0.78 with a 95% confidence interval of 0.75-0.89 versus 0.64 with a 95% confidence interval of 0.64-0.81, positive predictive value (PPV) (0.09 with a 95% confidence interval of 0.08-0.15 versus 0.05 with a 95% confidence interval of 0.05-0.08), and negative predictive value (NPV) (1.00 with a 95% confidence interval of 0.99-1.0 versus 0.99 with a 95% confidence interval of 0.99-0.99).

4. Advantages

Various embodiments of the present invention provide significant technical advantages and address technical challenges of determining an acuity score and/or mortality prediction for a patient during a medical event (e.g., ICU admission/stay, medical/surgical procedure, and/or the like). Moreover, various embodiments of the present invention provide the advantage of providing clinicians with important information regarding which parameters are the most important parameters corresponding to the determined acuity score and/or mortality prediction and whether or not those parameters represent therapeutic targets. Thus, various embodiments of the present invention provide clinicians with valuable and, in some embodiments, (near) real-time information/data regarding therapeutic targets that may most efficiently and/or effectively improve the patient's condition and expected outcome. Various embodiments of the deep learning model (a DeepSOFA model, in some embodiments) provide more accurate mortality predictions than various other traditional SOFA and/or regression models. Various embodiments thus provide a specific improvement over prior art systems by allowing a patient's EHR and/or clinicians attending to the patient to be updated in real time or near real time with a prediction (e.g., acuity score, mortality prediction, and/or the like) for a patient during a medical event evolving the patient such that clinicians can make fully informed decisions throughout the medical event.

Various embodiments of the present invention therefore provide a technical improvement to the field of acuity monitoring of patients throughout a medical event.

IV. CONCLUSION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation

The invention claimed is:

1. A method for providing a patient prediction, the method comprising:
   responsive to receiving an indication of initiation of a medical event for a patient, initiating a deep learning machine learning model for the patient, wherein the deep learning machine learning model (a) comprises a modified recurrent neural network (RNN) with gated recurrent units (GRUs) and a self-attention mechanism, (b) is executed by an assessment computing entity, (c) has been trained using machine learning, and (d) is configured to generate a prediction for the patient comprising at least one of an acuity score or a mortality prediction;
   responsive to determining that a configurable time period has elapsed since a previous execution of the deep learning machine learning model for the patient, identifying, by the assessment computing entity, a prediction trigger;
   responsive to identifying the prediction trigger, requesting, by the assessment computing entity, updated medical data for the patient;
   responsive to receiving the updated medical data for the patient, providing, by the assessment computing entity, the updated medical data as input to the deep learning machine learning model;
   executing, by the assessment computing entity, the deep learning machine learning model for the patient to cause the deep learning machine learning model to:
      determine a respective hidden state for each time step of one or more time steps of medical data, wherein each time step of medical data of the one or more time steps of medical data comprises a respective plurality of measurements corresponding to the time step and corresponding to the patient and the one or more times steps of medical data includes the update medical data,
      determine a respective attention parameter for each time step of the one or more time steps,
      determine a weighted average hidden state by aggregating a time series of respective weighted hidden states of the deep learning machine learning model for the patient, each respective weighted hidden state of the time series of respective weighted hidden states corresponding to a respective time step of the one or more time steps, wherein the respective weighted hidden state is determined based at least in part on a respective weight determined based at least in part on the respective attention parameter for a respective time step corresponding to the respective hidden state,
      wherein the self-attention mechanism determines the attention parameter for each time step of the one or more time steps and the attention parameter for a time step indicates an influence of the time step on the prediction, and
      automatically generate the prediction by providing the weighted average hidden state to a classification layer of the deep learning machine learning model;
   automatically providing, by the assessment computing entity, at least a portion of the prediction and a self-attention parameter distribution such that at least one of (a) the at least a portion of the prediction and the self-attention parameter distribution is used to update an electronic health record corresponding to the patient or (b) displaying to a clinician for review;
   determining an updated configurable time period based at least in part on the prediction; and
   responsive to determining that the updated configurable time period has elapsed since the prediction was determined, identifying another prediction trigger, requesting new medical data, receiving the new medical data in response to the request, and updating the deep learning machine learning model for the patient, based at least in part on the new medical data, to automatically determine and provide a new prediction and a new self-attention parameter distribution.

2. The method of claim 1, wherein the acuity score is a sequential organ failure assessment (SOFA) score.

3. The method of claim 1, wherein the prediction comprises at least one attention parameter and/or distribution of the respective attention parameters.

4. The method of claim 3, wherein the at least one attention parameter and/or distribution of the respective attention parameters is flagged as to whether or not the attention parameter and/or distribution of the respective attention parameters represents a therapeutic target.

5. The method of claim 1, wherein the at least a portion of the prediction is provided such that the at least a portion of the prediction is received by a user computing entity configured to provide the at least a portion of the prediction to the clinician for review.

6. The method of claim 1, wherein the at least a portion of the prediction is provided such that the at least a portion of the prediction is received by a records computing entity configured to update an electronic health record corresponding to the patient based at least in part on the at least a portion of the prediction.

7. The method of claim 1, wherein the medical event is at least one of an intensive care unit (ICU) stay, a medical procedure, or a surgical procedure.

8. The method of claim 1, further comprising receiving medical data provided via user interaction with one or more user computing entities and/or data collection via one or more sensors.

9. The method of claim 1, further comprising receiving medical data from a patient electronic health record (EHR).

10. The method of claim 1, wherein the at least one of the acuity score or the mortality prediction is a real-time acuity score or mortality prediction for the patient.

11. The method of claim 1, wherein the deep learning machine learning model comprises a static module for receiving and processing background information corresponding to the patient and a time series module for receiving and processing the medical data corresponding to the patient.

12. The method of claim 1, wherein a sum of the respective attention parameters for the one or more time steps is one.

13. The method of claim 1, wherein initiating the deep learning machine learning model for the patient comprises accessing information from a patient electronic health record (EHR) corresponding to the patient and setting an initial time step of medical data of the one or more time steps of medical data based on the information from the patient EHR.

14. An apparatus comprising at least one processor, a communications interface configured for communicating via at least one network, and at least one memory storing computer program code, the at least one memory and the computer program code configured to, with the processor, cause the apparatus to at least:

responsive to receiving an indication of initiation of a medical event, initiate a deep learning machine learning model for a patient, wherein the deep learning machine learning model (a) comprises a modified recurrent neural network (RNN) with gated recurrent units (GRUs) and a self-attention mechanism, (b) is executed by an assessment computing entity, (c) has been trained using machine learning, and (d) is configured to generate a prediction for the patient comprising at least one of an acuity score or a mortality prediction;

responsive to determining that a configurable time period has elapsed since a previous execution of the deep learning machine learning model for the patient, identify a prediction trigger;

responsive to identifying the prediction trigger, request updated medical data for the patient;

responsive to receiving the updated medical data for the patient, provide the updated medical data as input to the deep learning machine learning model;

execute the deep learning machine learning model for the patient to cause the deep learning machine learning model to:

determine a respective hidden state for each time step of one or more time steps of medical data, wherein each time step of medical data of the one or more time steps of medical data comprises a respective plurality of measurements corresponding to the time step and corresponding to the patient and the one or more times steps of medical data includes the update medical data, determine a respective attention parameter for each time step of the one or more time steps, determine a weighted average hidden state by aggregating a time series of respective weighted hidden states of the deep learning machine learning model for the patient, each respective weighted hidden state of the time series of respective weighted hidden states corresponding to a respective time step of the one or more time steps, wherein the respective weighted hidden state is determined based at least in part on a respective weight determined based at least in part on the respective attention parameter for a respective time step corresponding to the respective hidden state, wherein the self-attention mechanism determines the attention parameter for each time step of the one or more time steps and the attention parameter for a time step indicates an influence of the time step on the prediction, and automatically generate the prediction by providing the weighted average hidden state to a classification layer of the deep learning machine learning model;

automatically provide at least a portion of the prediction and a self-attention parameter distribution such that at least one of (a) the at least a portion of the prediction and the self-attention parameter distribution is used to update an electronic health record corresponding to the patient or (b) displaying to a clinician for review;

determine an updated configurable time period based at least in part on the prediction; and responsive to determining that the updated configurable time period has elapsed since the prediction was determined, identify another prediction trigger, request new medical data, receive the new medical data in response to the request, and update the deep learning machine learning model for the patient, based at least in part on the new medical data, to automatically determine and provide a new prediction and a new self-attention parameter distribution.

15. The apparatus of claim 14, wherein the deep learning machine learning model comprises a static module for receiving and processing background information corresponding to the patient and a time series module for receiving and processing the medical data corresponding to the patient.

16. The apparatus of claim 14, wherein the prediction comprises at least one attention parameter and/or distribution of the respective attention parameters.

17. The apparatus of claim 16, wherein the at least one attention parameter and/or distribution of the respective attention parameters is flagged as to whether or not the attention parameter and/or distribution of the respective attention parameters represents a therapeutic target.

18. The apparatus of claim 14, wherein the at least a portion of the prediction is provided such that the at least a portion of the prediction is received by a user computing entity configured to provide the at least a portion of the prediction to the clinician for review.

19. The apparatus of claim 14, wherein the at least a portion of the prediction is provided such that the at least a portion of the prediction is received by a records computing entity configured to update an electronic health record corresponding to the patient based at least in part on the at least a portion of the prediction.

20. A computer program product comprising at least one non-transitory computer-readable storage medium having computer-readable program code portions stored therein, the computer-readable program code portions comprising executable portions configured, when executed by a processor of an apparatus, to cause the apparatus to:

responsive to receiving an indication of initiation of a medical event, initiate a deep learning machine learning model for a patient, wherein the deep learning machine learning model (a) comprises a modified recurrent neural network (RNN) with gated recurrent units (GRUs) and a self-attention mechanism, (b) is executed by an assessment computing entity, (c) has been trained using machine learning, and (d) is configured to generate a prediction for the patient comprising at least one of an acuity score or a mortality prediction;

responsive to determining that a configurable time period has elapsed since a previous execution of the deep learning machine learning model for the patient, identify a prediction trigger;

responsive to identifying the prediction trigger, request updated medical data for the patient;

responsive to receiving the updated medical data for the patient, provide the updated medical data as input to the deep learning machine learning model;

execute the deep learning machine learning model for the patient to cause the deep learning machine learning model to:

determine a respective hidden state for each time step of one or more time steps of medical data, wherein each time step of medical data of the one or more time steps of medical data comprises a respective plurality of measurements corresponding to the time step and corresponding to the patient and the one or more times steps of medical data includes the update medical data, determine a respective attention parameter for each time step of the one or more time steps, determine a weighted average hidden state by aggregating a time series of respective weighted hidden states of the deep learning machine learning model for the patient, each respective weighted hidden state of the time series of respective weighted hidden states corresponding to a respective time step of the one or more time steps, wherein the respective weighted hidden state is determined based at least in part on a respective weight determined based at least in part on the respective attention parameter for a respective time step corresponding to the respective hidden state, wherein the self-attention mechanism determines the attention parameter for each time step of the one or more time steps and the attention parameter for a time step indicates an influence of the time step on the prediction, and automatically generate the prediction by providing the weighted average hidden state to a classification layer of the deep learning machine learning model;

automatically provide at least a portion of the prediction and a self-attention parameter distribution such that at least one of (a) the at least a portion of the prediction and the self-attention parameter distribution is used to update an electronic health record corresponding to the patient or (b) displaying to a clinician for review;

determine an updated configurable time period based at least in part on the prediction; and responsive to determining that the updated configurable time period has elapsed since the prediction was determined, identify another prediction trigger, request new medical data, receive the new medical data in response to the request, and update the deep learning machine learning model for the patient, based at least in part on the new medical data, to automatically determine and provide a new prediction and a new self-attention parameter distribution.

\* \* \* \* \*

UNITED STATES PATENT AND TRADEMARK OFFICE
CERTIFICATE OF CORRECTION

| | | |
|---|---|---|
| PATENT NO. | : 12,340,905 B2 | Page 1 of 1 |
| APPLICATION NO. | : 17/309975 | |
| DATED | : June 24, 2025 | |
| INVENTOR(S) | : Azra Bihorac et al. | |

It is certified that error appears in the above-identified patent and that said Letters Patent is hereby corrected as shown below:

In the Specification

<u>Column 1, Lines 19-23:</u>
The paragraph that reads:
"This invention was made with government support under Grant No. 1750192 awarded by the National Science Foundation and Grant Nos. GM111152 and GM110240 awarded by the National Institutes of Health. The government has certain rights in the invention."

Should read:
-- This invention was made with government support under Grant No(s). R01 GM110240, R01 GM149657, P50 GM111152, awarded by the National Institutes of Health; and Grant No. 1750192, awarded by the National Science Foundation. The government has certain rights in the invention. --

Signed and Sealed this
Tenth Day of February, 2026

John A. Squires
*Director of the United States Patent and Trademark Office*